United States Patent [19]
Kruper, Jr. et al.

[11] Patent Number: 5,310,535
[45] Date of Patent: May 10, 1994

[54] CARBOXAMIDE MODIFIED POLYAMINE CHELATORS AND RADIOACTIVE COMPLEXES THEREOF FOR CONJUGATION TO ANTIBODIES

[75] Inventors: William J. Kruper, Jr., Sanford; William A. Fordyce, Midland, both of Mich.; A. Dean Sherry, Dallas, Tex.

[73] Assignees: The Dow Chemical Company, Midland, Mich.; The University of Texas, Austin, Tex.

[21] Appl. No.: 874,244

[22] Filed: Apr. 24, 1992

[51] Int. Cl.$^5$ .................. A61K 43/00; A61K 49/02
[52] U.S. Cl. .................................................. 424/1.53
[58] Field of Search ................ 424/1.1, 9; 600/3; 534/10, 15, 16; 540/470, 474

[56] References Cited

U.S. PATENT DOCUMENTS

| | | | |
|---|---|---|---|
| 4,647,447 | 3/1987 | Gries et al. | 424/9 |
| 4,678,667 | 7/1987 | Meares et al. | 424/85 |
| 4,885,363 | 12/1989 | Tweedle et al. | 540/465 |
| 4,923,985 | 5/1990 | Gansow | 540/474 |
| 4,957,939 | 9/1990 | Gries et al. | 514/492 |
| 4,963,344 | 10/1990 | Gries et al. | 424/9 |
| 4,994,560 | 2/1991 | Kruper, Jr. et al. | 534/10 |
| 5,049,667 | 9/1991 | Schaefer et al. | 540/474 |
| 5,057,302 | 10/1991 | Johnson et al. | 424/1.1 |

FOREIGN PATENT DOCUMENTS

| | | |
|---|---|---|
| 0238196 | 2/1987 | European Pat. Off. |
| 0325762 | 12/1988 | European Pat. Off. |
| 0327365 | 2/1989 | European Pat. Off. |
| 0382582 | 2/1990 | European Pat. Off. |
| 0382583 | 2/1990 | European Pat. Off. |
| 8901476 | 8/1988 | PCT Int'l Appl. |
| 8912631 | 12/1989 | PCT Int'l Appl. |

OTHER PUBLICATIONS

Pier S. Pallavicini et al.; J. Am. Chem. Soc. 1987, 109, pp. 5139–5144; "*N-(Aminoethyl)cyclam: A Tetraaza Macrocycle with a Coordinating Tail (Scorpiand) . . .*".

Th. A. Kaden et al; Pure & Appl. Chem., vol. 61, No. 5, pp. 879–883, 1989; "*Reactivity of side chain functional groups in macrocyclic $Cu^{2+}$ complexes*".

Hiroshi Tsukube; J. Chem. Soc. Perkin Trans I 1989, pp. 1537–1538; Perkin Communications; "*Amide armed Azamacrocycles as a New Series of Synthetic Carriers for Alkali . . .*".

Markus Hediger et al.; J.C.S. Chem. Comm., 1978; pp. 14–15; "*Synthesis and Metal Complexes of Mono-N-substituted Tetra-azamacrocycles*".

A. Dean Sherry; Inorg. Chem. 1989, 28, pp. 620–622; "*Synthesis and Characterization of the Gadolinium (3+) Complex of DOTA-Propylamide: A Model DOTA–Protein Conjugate*".

Primary Examiner—Robert L. Stoll
Assistant Examiner—Lara E. Chapman

[57] ABSTRACT

A group of functionalized polyaminocarboxamide modified chelators that form complexes with rare earth-type metal ions are disclosed. The complexes, covalently attached to an antibody or antibody fragment, can be used for therapeutic and/or diagnostic purposes.

6 Claims, No Drawings

CARBOXAMIDE MODIFIED POLYAMINE CHELATORS AND RADIOACTIVE COMPLEXES THEREOF FOR CONJUGATION TO ANTIBODIES

BACKGROUND OF THE INVENTION

The present invention relates to novel charge modified chelators useful to attach radioactive metal ions to tumor selective antibodies.

Functionalized chelants, or bifunctional coordinators, are known to be capable of being covalently attached to an antibody having specificity for cancer or tumor cell epitopes or antigens. Radionuclide complexes of such antibody/chelant conjugates are useful in diagnostic and/or therapeutic applications as a means of conveying the radionuclide to a cancer or tumor cell. See, for example, Meares et al., *Anal. Biochem.*, 124, 68–78 (1984); and Krejcarek et al., *Biochem and Biophys. Res. Comm.*, 77, 581–585 (1977).

Attachment of the metal ion to a protein such as an antibody has been achieved by complexation by an acyclic chelate such as carboxymethylated amine derivatives of ethylenediaminetetraacetic acid (EDTA) (U.S. Pat. No. 4,662,420) or diethylenetriaminepentaacetic acid (DTPA) (U.S. Pat. Nos. 4,479,930 and 4,454,106), covalently linked to the antibody. Such acyclic complexes, however, tend to be unstable in vivo either as a result of acid-catalyzed decomplexation or competitive chelate binding by calcium or zinc in serum. The lack of stability can result in uncomplexed metal atoms in the body which have a cytotoxic effect on healthy tissue (e.g., bone marrow).

An alternative to the use of acyclic chelates for the labeling of antibodies is the use of macrocyclic ligands. Certain macrocyclic bifunctional chelating agents and the use of their copper chelate conjugates for diagnostic or therapeutic applications have been disclosed in U.S. Pat. No. 4,678,667 and by Moi et al., *Inorg. Chem.*, 26, 3458≈3463 (1987). Attachment of the aminocarboxylic acid functionality to the rest of the bifunctional chelating molecule is through a ring carbon of the cyclic polyamine backbone. Thus, a linker attached at one end to a ring carbon of the cyclic polyamine, is also attached at its other end to a functional group capable of reacting with the protein.

Tetraazamacrocycles which can act as bifunctional chelating agents for use in diagnosis and therapy are described in published European Patent Application 0 382 582, on Aug. 16, 1990. At least one of the side arms emanating from an amine of the ring being a phosphinate ester. The linker group being attached to a ring carbon of the tetraazamacrocycle.

U.S. Pat. No. 4,994,560 discloses rhodium complexed to bifunctional chelators containing a polyamine, wherein the polyamine chelating agent can be a polyazamacrocycle, where the linker group is covalently attached to any one of the carbon or nitrogen atoms of the polyamine. Such polyamines form outstandingly inert complexes with rhodium (III), but are inappropriate for the radiochelation of lanthanide (III) metal ions.

Carboxymethylated tetraazamacrocycles have been described which are capable of forming inert complexes with copper and lanthanide metal ions and can be conjugated to antibodies [WO 87/050309 WO 89/01476 and Moi et al., *J. Am Chem. Soc.*, 110, 6266 (1988)]. Published PCT Application WO 89/02788 describes bifunctional chelators wherein a number of the secondary amine groups are carboxymethylated.

The present invention provides carboxymethylated tetrazamacrocycles, wherein one or two of the carboxylates are replaced with carboxamides. These chelating agents are antibody conjugatable and form complexes with lanthanides and other substitutionally labile metal ions which are kinetically inert. Upon metabolism of the antibody conjugate, these chelates exhibit rapid whole body clearance, and in certain cases have unexpectedly lower propensity for uptake in bone. Lower bone uptake would be expected to result in a less toxic radiopharmaceutical. The chelates also rapidly form chelate-protein conjugates.

SUMMARY OF THE INVENTION

The present invention is directed to novel bifunctional chelating agents that form complexes with metal ions, especially "radioactive" metal ions having rare earth-type chemistry. The complexes so formed can be covalently attached to an antibody or antibody fragment to form conjugates and used for therapeutic and/or diagnostic purposes. The complexes and/or conjugates can be formulated for en vivo or in vitro uses. A preferred use of the formulated conjugates is the treatment of cancer in animals, especially humans.

Uses of the complexes and/or conjugates of this invention which contain a non-radioactive metal for diagnosis and/or treatment of disease states, such as cancer are also possible. See, for example, K. Pettersson et al., *Clinical Chemistry*, 299 60–64 (1983) and C. Meares et al., *Acc. Chem. Res.*, 17, 202–209 (1984), for a discussion of fluorescent-immunoguided therapy.

More specifically, the present invention is directed to a compound of the formula:

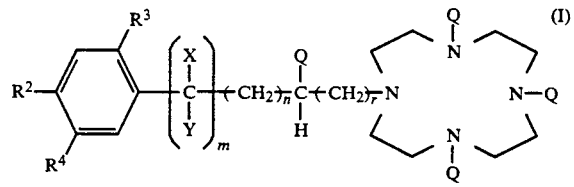

wherein:
each Q is independently hydrogen, $(CHR^5)_pCO_2R$; or $(CHR^5)_9C(O)N(R^6)_2$ with the proviso that at least one Q is $(CHR^5)_pC(O)N(R^6)_2$;
R at each occurrence is independently hydrogen, benzyl or $C_1$–$C_4$ alkyl;
each $R^5$ independently is hydrogen, $C_1$–$C_4$ alkyl or -($C_1$–$C_2$ alkyl)phenyl;
each $R^6$ independently is hydrogen, $C_1$–$C_9$ alkyl, or -($C_1$–$C_2$ alkyl)phenyl;
X and Y are each independently hydrogen or may be taken with an adjacent X and Y to form an additional carbon-carbon bond to produce an alkene or alkyne;
n is 0 or 1;
m is an integer from 0 to 10 inclusive;
p=1 or 2;
r=0 or 1;
with the proviso that n is only 1 when X and/or Y form an additional carbon-carbon bond,
$R^2$ and $R^4$ are independently hydrogen, amino, isothiocyanato, semicarbazido, thiosemicarbazido, maleimido, bromoacetamido or carboxyl;

$R^3$ is $C_1$–$C_4$ alkoxy, —$OCH_2CO_2H$, hydroxy or hydrogen;

with the proviso that $R^2$ and $R^4$ cannot both be hydrogen but one of $R^2$ and $R^4$ must be hydrogen; or a pharmaceutically acceptable salt thereof.

As used herein the term "alkyl" means a linear or branched alkyl.

The present invention is also directed to rare-earth type metal ion complexes, especially radioactive neutral or charged rare-earth type metal ion complexes, and to conjugates formed with the aforementioned complexes and antibody or antibody fragments. The term "radioactive" means a metal ion that emits particles and/or electromagnetic radiation from the nucleus. The use of the amide-modified side arms offer advantages over chelating agents known in the prior art which contain carboxylated side arms in that the chelating agents containing the amide-modified side arms can be conjugated to proteins, such as antibodies, under more mild conditions. The rapid formation of the conjugate is of importance in production of a radiochemical compound for therapeutic and/or diagnostic purposes.

It has also been found that the chelating agents of the present invention, which contain one amide-modified side arm, have a lower propensity for uptake in the bone than do chelating agents known in the prior art such as 1,4,7,10-tetraazacyclododecane-1,4,7,10-tetraacetic acid and bifunctional derivatives thereof.

In addition, the present invention also includes formulations having the conjugates of the invention and a pharmaceutically acceptable carrier, especially formulations where the pharmaceutically acceptable carrier is a liquid. The invention also includes a method for the diagnosis or treatment of a disease state, especially cancer, in a mammal which comprises administering to the mammal an effective amount of the formulation. The term "mammal" includes especially humans.

DETAILED DESCRIPTION OF THE INVENTION

As used herein, the term "chelating agent" means a compound capable of chelating or sequestering a metal ion. The term "chelate" means a chelating agent which has chelated or sequestered a metal ion.

The term "bifunctional chelating agent" means a compound that has a moiety capable of chelating a metal ion and a linker/spacer moiety covalently bonded to the chelating moiety that is capable of being activated or functionalized to serve as a means to covalently attach to a biological molecule.

The term "biological molecule" refers to any protein, antibody, antibody fragment, hormone, antigen or hapten which functions to recognize a specific biological target site. Such a biological molecule, when attached to a functionalized chelate, serves to carry the attached metal ion to specific targeted tissues. Preferably, the biological material is an antibody or antibody fragment.

As used herein, "antibody" refers to any polyclonal, monoclonal, chimeric antibody or heteroantibody, preferably a monoclonal antibody. The term "antibody fragment" includes Fab fragments and F(ab')2 fragments and any portion of an antibody having specificity toward a desired epitope or epitopes.

The term "conjugate" as used herein refers to a complex of a biological material attached to a bifunctional chelating agent or bifunctional chelate. The term "antibody/chelate conjugate" refers to an antibody which is covalently attached to a bifunctional chelate (i.e., the bifunctional chelating agent having a chelated metal ion).

Metals which can form complexes with the bifunctional chelating agents of the present invention include La, Ce, Pr, Nd, Pm, Sm, Eu, Gd, Tb, Dy, Ho, Er, Tm, Yb, Lu, Y and Sc. Preferred radioactive rare earth-type metal ions include $^{153}Sm$, $^{166}Ho$, $^{90}Y$, $^{149}Pm$, $^{159}Gd$, $^{140}La$, $^{177}Lu$, $^{175}Yb$, $^{47}Sc$, and $^{142}Pr$. Other radioactive metal ions which may be of interest are $^{47}Sc$, $^{99m}Tc$, $^{186}Re$, $^{188}Re$, $^{97}Ru$, $^{105}Rh$, $^{109}Pd$, $^{197}Pt$, $^{67}Cu$, $^{198}Au$, $^{199}Au$, $^{67}Ga$, $^{68}Ga$, $^{111}In$, $^{113m}In$, $^{115m}In$, $^{117}Sn$, and $^{212}Pb/^{212}Bi$. When the term "radioactive" is used in conjunction with the word "metal ion", it refers to one or more isotopes of the rare-earth type elements that emit particles and/or photons, such as $^{153}Sm$, $^{166}Ho$, $^{90}Y$, $^{149}Pm$, $^{159}Gd$, $^{140}La$, $^{177}Lu$, $^{175}Yb$, $^{47}Sc$, and $^{142}Pr$.

As used herein, "pharmaceutically-acceptable salt" means any salt of a compound of Formula (I) which is sufficiently non-toxic to be useful in therapy or diagnosis of mammals. Thus, the salts are useful in accordance with this invention. Representative of those salts, which are formed by standard reactions, from both organic and inorganic sources include, for example, sulfuric, hydrochloric, phosphoric, acetic, succinic, citric, lactic, maleic, fumaric, palmitic, cholic, palmoic, mucic, glutamic, d-camphoric, glutaric, glycolic, phthalic, tartaric, formic, lauric, steric, alicylic, methanesulfonic, benzenesulfonic, sorbic, picric, benzoic, cinnamic acids and other suitable acids. Also included are salts formed by standard reactions from both organic and inorganic sources such as ammonium, alkali metal ions, alkaline earth metal ions, and other similar ions. Particularly preferred are the salts of the compounds of Formula (I) where the salt is chloride or the salt of an anionic buffer such as acetate, or mixtures thereof.

Preferred compounds of Formula (I) include those compounds where X and Y are each H and r is 0 as shown by the following formula:

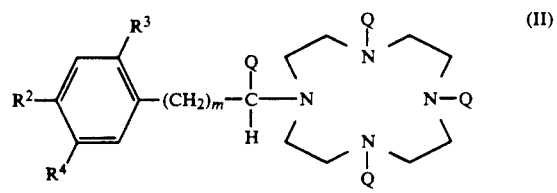

(II)

wherein:
each Q is independently hydrogen, $(CHR^5)_p CO_2R$; or $(CHR^5)_p C(O)N(R^6)_2$; with the proviso that at least one Q is $(CHR^5)_p C(O)N(R^6)_2$;

R at each occurrence is independently hydrogen, benzyl or $C_1$–$C_4$ alkyl;

m is an integer from 0 to 5 inclusive;

p is 1 or 2;

$R^2$ and $R^4$ are independently hydrogen, amino, isothiocyanato, semicarbazido, thiosemicarbazido, carboxyl, bromoacetamido or maleimido;

$R^3$ is $C_1$–$C_4$ alkoxy, —$OCH_2CO_2H$, hydroxy or hydrogen;

each $R^5$ independently is hydrogen or $C_1$–$C_4$ alkyl;

each $R^6$ independently is hydrogen, $C_1$–$C_9$ alkyl, or -($C_1$–$C_2$ alkyl)phenyl;

with the proviso that $R^2$ and $R^4$ cannot both be hydrogen but one of $R^2$ and $R^4$ must be hydrogen; or a pharmaceutically acceptable salt thereof.

The bifunctional chelating agents described herein [represented by either of Formula (I) or (II)] can be used to chelate or sequester the rare-earth type metal ions, particularly radioactive rare-earth type metal ions, so as to form metal ion chelates (also referred to herein as "complexes"). The complexes, because of the presence of the functionalizing moiety [represented by 1IR2,, or "R4,, in Formula (I) or (II)], can be attached to functionalized supports, such as functionalized polymeric supports, or preferably can be covalently attached to proteins, or more specifically to antibodies or antibody fragments. Thus, the complexes described herein (represented by either of Formula I or II complexed with rare-earth type metal ions, particularly radioactive rare-earth type metal ions) may be covalently attached to an antibody or antibody fragment and are referred to herein as "conjugates".

The antibodies or antibody fragments which may be used in the conjugates described herein can be prepared by techniques well known in the art. Highly specific monoclonal antibodies can be produced by hybridization techniques well known in the art, see, for example, Kohler and Milstein [Nature, 256, 495–497 (1975); and *Eur. J. Immunol.*, 6, 511–519 (1976)]. Such antibodies normally have a highly specific reactivity. In the radioactive metal ion conjugates, antibodies directed against any desired antigen or hapten may be used. Preferably, the antibodies which are used in the radioactive metal ion conjugates are monoclonal antibodies, or fragments thereof having high specificity for a desired epitope(s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Some examples of antibodies or antibody fragments are CC-11, CC-46, CC-49, CC-49 F(ab')$_2$, CC-83, CC-83 F(ab')$_2$, and B72.3- [See D. Colcher et al., *Cancer Res.*, 48, 4597–4603 (Aug. 15, 1988) for CC-49, CC-83 and B72.3 antibodies. The hybridoma cell line B72.3 is deposited in the American Type Culture Collection (ATCC) having the accession number HB 8108. The various CC antibodies are disclosed in published PCT Application WO 89/00692, on Jan. 26, 1989 and published PCT Application WO 90/04410, on May 3, 1990. The other murine monoclonal antibodies bind to epitopes of TAG-72, a tumor associated antigen. A more complete list of antigens can be found in U.S. Pat. No. 4,193,983, which is incorporated herein by reference. The radioactive metal ion conjugates of the present invention are particularly preferred for the diagnosis and treatment of various cancers.

Methods for chelating the metal ion with the chelating agent of the present invention are known in the art. The metal ion can be complexed with the chelating agent or bifunctional chelating agent by adding the chelating agent or bifunctional chelating agent to a solution of the radionuclide. Chelates form readily upon mixing in an aqueous solution at a pH of about 1 to about 10. Preferably, the reaction is carried out in a medium having a pH of about 5 to about 7. Ambient temperatures of about 20° C. to about 27° C. can be readily employed for metal ion chelation. The amount of metal ion employed may be from trace amounts to an amount exceeding equimolar with the chelate.

The conjugates of the present invention are preferably prepared by first forming the chelate and then binding the antibody or antibody fragment. Thus, the process involves preparing or obtaining the ligand, forming the complex with the metal and then adding the antibody. Alternatively, a process for making labeled antibody conjugates can involve first conjugation of the bifunctional chelator to the antibody and its subsequent chelation to yield the radionuclide-BFC labeled antibody. Any suitable process that results in the formation of the conjugates of this invention is within the scope of this invention.

The chelating agents of the present invention containing the amide-modified side arms have been found to conjugate with antibodies under mild conditions more rapidly than chelating agents containing only carboxylated side arms. The rapid conjugation is advantageous in producing radiochemical conjugates for therapeutic and/or diagnostic purposes in that a shortened conjugation time reduces the amount of radiolysis and reduces formation of by-products, such as antibody aggregates and chelate degradation products.

The conjugates of this invention, and in some instances the complexes of this invention, may be employed as a formulation. The formulation comprises a compound of Formula (I) with the antibody and/or metal ion and a physiologically-acceptable carrier, excipient or vehicle therefore. Thus, the formulation may consist of a physiologically-acceptable carrier with a complex (metal ion +ligand), conjugate (metal ion +ligand +antibody) or (ligand +antibody). The methods for preparing such formulations are well known. The formulation may be in the form of a suspension, injectable solution or other suitable pharmaceutical formulation. Physiologically-acceptable suspending media, with or without adjuvants, may be used.

The formulations of the present invention are in the solid or liquid form containing the active radionuclide complexed with the ligand. These formulations may be in kit form such that the two components (i.e., ligand and metal, complex and antibody, or ligand/antibody and metal) are mixed at the appropriate time prior to use. Whether premixed or as a kit, the formulations usually require a pharmaceutically-acceptable carrier.

Injectable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically-acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50 percent of the organic solvent by volume.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Physiologically-acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters.

Many substances which effect the hydrophilicity, density, and surface tension of the liquid suspension medium can assist in making injectable suspensions in individual cases. For example, silicone antifoams, sorbitol, and sugars are all useful suspending agents.

An "effective amount" of the formulation is used for therapy. The dose will vary depending on the disease being treated. Although in vitro diagnostics can be performed with the formulations of this invention, in vivo diagnostics are also contemplated. The conjugates and formulations of this invention can also be used in radioimmuno guided surgery (RIGS); however, other metals which could be used for this purpose also include $^{99m}Tc$, $^{111}In$, $^{113m}In$, $^{67}Ga$ and $^{68}Ga$.

Other uses of some of the chelants of the present invention may include magnetic resonance imaging, e.g., the complexes of Formula I, especially complexes of Formula VI, with $Gd^{+3}$, attachment to polymeric supports for various purposes, e.g., as diagnostic agents, and removal of lanthanide metal or pseudo-lanthanide metal ion by selective extraction.

Synthetic routes to add a linker moiety to the twelve-membered macrocyclic (e.g., the free-base macrocycle, 1,4,7,10-tetraazacyclododecane), which would allow covalent attachment of the bifunctional ligand to a protein, are disclosed in U.S. patent application, Ser. No. 07/370,956, by Cheng et al., filed Jun. 21, 1989, the disclosure of which is hereby incorporated by reference. In general, the process involves reacting a polyazamacrocycle with between about one to three equivalents of an appropriate electrophile (e.g., any appropriately substituted α-halocarboxylic acid ester) in a solvent which will not promote a proton transfer to produce a mono-N-functional polyazamacrocycle, as disclosed in U.S. Pat. No. 5,064,956, the disclosure of which is hereby incorporated by reference.

The preparation of substituted α-haloacid esters, used as starting materials, is well known in the art. One approach involves bromination or chlorination of the acid halide generated in situ, e.g., D. N. Harpp et al., *J. Org. Chem.*, 40, 3420-27 (1975). This approach allows for exclusive alpha-halogenation of alkanoic acids which may contain reactive benzylic groups. A general method to substitute acid halides involves reaction of the organic acid with thionyl chloride or sulfuryl chloride, e.g., E. Schwenk et al., *J. Amer. Chem Soc.*, 70, 3626-27 (1944). Both methods utilize the free carboxylic acid which is frequently available from commercial sources.

Polyazamacrocycles such as 1,4,7,10-tetraazacyclododecane may be prepared by methods known in the art, such as, T. J. Richman et al., *Org. Synthesis*, 58, 86-98 (1978).

Carboxylation of the mono-N-functional macrocycle may be performed by the method of Desreux using bromoacetic acid derivatives and a suitable base [J. F. Desreux, *Inorg. Chem.*, 19, 1319-24 (1980)].

Benzyl, or preferentially t-butyl ester of bromoacetic acid, should be employed since purification of the resulting ester containing product is straightforward using silica gel chromatography. Importantly, removal of the labile ester group after purification is effected by hydrolysis with mineral acid (aqueous hydrochloride at 30° to 40° C.) under mild reaction conditions which preserves the amide functional group. Surprisingly, the analogous methyl ester of 5 could not be hydrolyzed without loss of the amide group.

The addition of the amide side arm to the polyazamacrocycle may be done by reacting an α-haloamide with the polyazamacrocycle in a suitable organic solvent, such as chloroform. The procedures for preparing an α-haloamide typically involves reacting a primary or secondary amine with an α-haloacid halide and are well known in the art.

All of the starting materials required for preparing the compounds of this invention are either available from commercial sources or can be made from known literature reference descriptions.

A general synthetic approach to produce the chelators of the present invention wherein one of Q groups is a carboxamide is given in the following Scheme I. Although only one compound is indicated by the terms shown, other similar moieties within Formula (I) where r=0 or 1, n=0 or 1, and m=0 through 10 can also be prepared by this method.

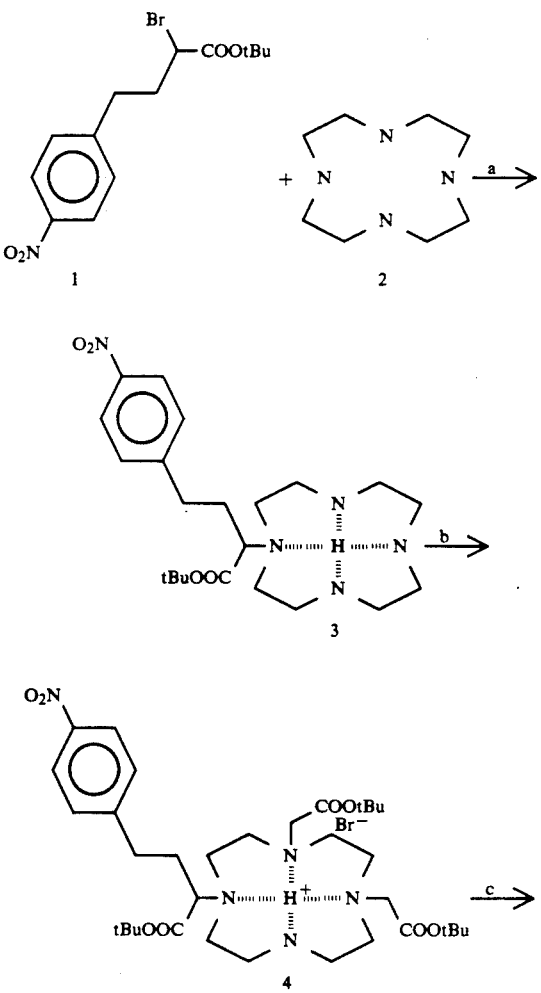

SCHEME 1: SYSTHESIS OF PA-DOTAMA

-continued
SCHEME 1: SYSTHESIS OF PA-DOTAMA

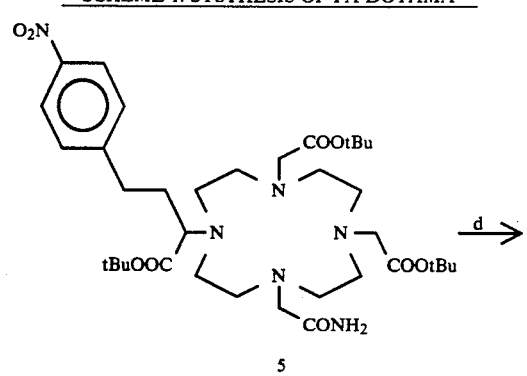

5

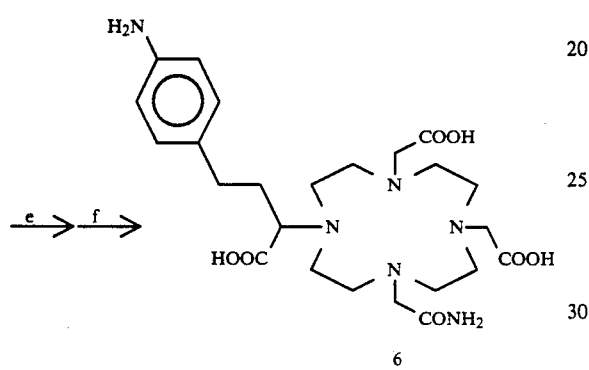

6

(a) 1.3 eq 2, CHCl₃ (78% chrom)
(b) 2.05 eq t-butyl bromoacetate, Hunig's Base, CHCl₃ (28% chrom);
(c) 1.1 eq bromoacetamide, Hunig's Base, CHCl₃ (90%)
(d) 10% Pd/C, H₂ (1 atm), ethanol, H₂O (100%)
(e) 6N HCL, 35–40 C (100%)
(f) Acid Washed Silica Chrom (50%)

In the following Scheme II, the compounds of formula (I) are prepared where two of the Q groups are carboxamides. Although only one compound is indicated by the terms shown, other similar moieties within Formula (I) where r=0 or 1, n=0 or 1, and m=0 through 10 can also be prepared by this method.

SCHEME 2: SYNTHESIS OF PA-DODADA

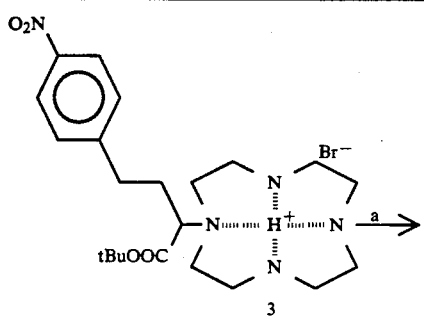

3

SCHEME 2: SYNTHESIS OF PA-DODADA

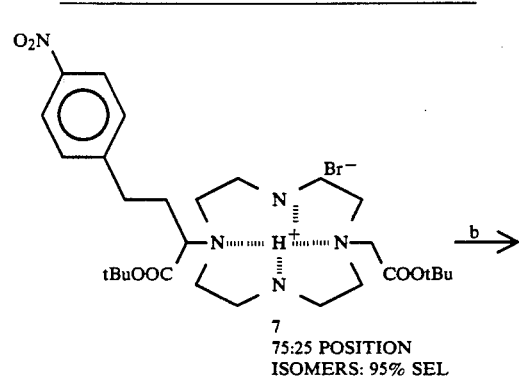

7
75:25 POSITION
ISOMERS: 95% SEL

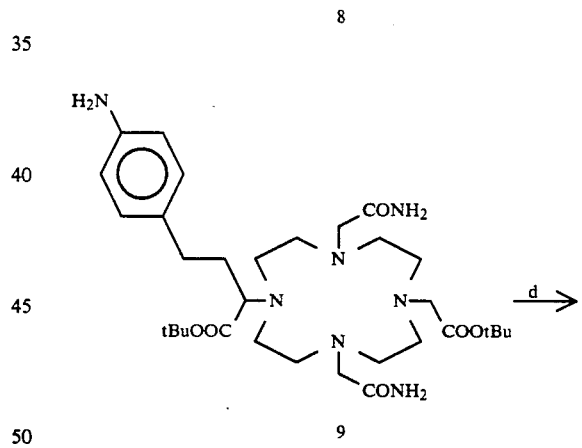

8

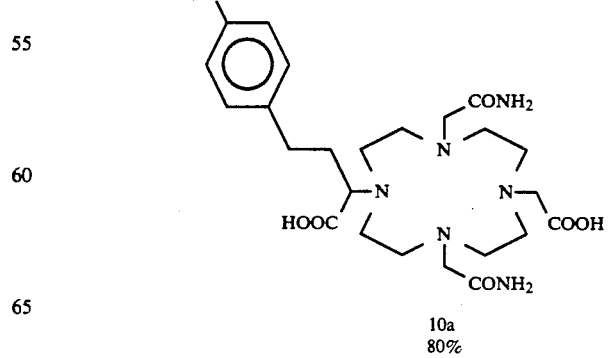

9

10a
80%

-continued
SCHEME 2: SYNTHESIS OF PA-DODADA

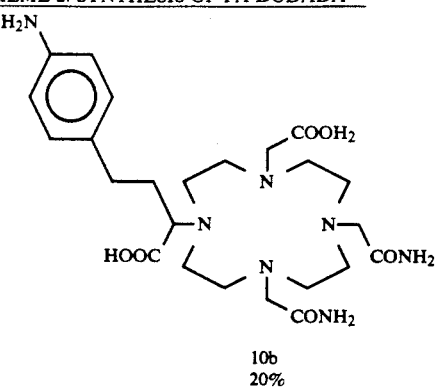

10b
20%

(a) 1.05 eq t-butyl bromoacetate, CHCl₃ Δ (38% chrom)
(b) 2.3 eq bromoacetamide, Hunig's Base, CHCl₃ (100%)
(c) 10% Pd/C, H₂ (1 atm), ethanol, H₂O (100%)
(d) 6N HCl, 35°-40° C. (100%); Acid Washed Silica Chrom (50%)

Radionuclides can be produced in several ways. In a nuclear reactor a nuclide is bombarded with neutrons to obtain a radionuclide, e.g.,

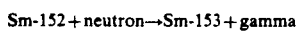

Sm-152 + neutron → Sm-153 + gamma

Another method of obtaining radionuclides is to bombard nuclides with particles in a linear accelerator or a cyclotron. Yet another way is to isolate the radionuelide from a mixture of fission products. The method of obtaining the nuclides employed in the present invention is not critical thereto.

The invention will be further clarified by a consideration of the following examples, which are intended to be purely exemplary of the present invention.

Glossary

BFC = bifunctional chelator
DTPA = diethylenetriaminepentaacetic acid
HEPES = N-2-hydroxyethylpiperazine-N'-2-ethane-sulfonic Acid
HPLC = high performance liquid chromatography
IRMA = immuno-radio-metric assay
PA-DODADA = 1,4,7,10-tetraaza-1-N-(1-carboxy-3-(4-aminophenyl)propyl)-7-N-(1-carboxymethyl)bis-4,10-N,N-(carboxamidomethyl)cyclododecane
PA-DOTA = 1-[2-(4-aminophenyl) ethyl]-1,4,7,10-tetraazacyclododecane-1,4,7,10-tetraacetic acid
PA-DOTAMA = 1,4,7,10-tetraaza-1-N-(carboxy-3-(4-nitrophenyl)propyl)-bis-4,7-N,N(carboxymethyl)-10-N-carboxamidomethyl)cyclododecane
PBS = phosphate buffered saline (containing 120 mM NaCl, 2.7 mM KCl, and 10 mM phosphate, PH 7.4)
SCN = isothiocyanato
TLC = thin layer chromatography

General Experimental

Mass spectra were obtained on a VG ZAB-MS high resolution mass spectrometer (Positive Ion Fast Atom Bombardment with Xenon using a matrix of dithioerthyritol/dithiothreitol—"Magic Bullet"—unless otherwise noted). ¹H and ¹³C NMR spectra were obtained using a Varian VXR-300 spectrometer. Infrared spectra (IR) were recorded on a Nicolet SSX FT/IR or Beckman Acculab instrument.

Elemental analyses are reported for the major chromatographed product without further purification unless noted, and were determined by using a Perkin Elmer 2400 CHN analyzer. All samples were vacuum dried (50°-600° C. at 10⁻¹ mm) overnight immediately prior to analysis.

All solvents employed were HPLC grade materials which were used without further purification. All preparative chromatography of organic compounds were performed using the flash chromatography technique described in the literature (Still, C. W.; Kahn, M.; Mitra, A., J. Org. Chem., 1978, 43, pp. 2923-2924.) (Merck Grade 60, 230-400 mesh silica gel, 60A-Aldrich Chemical Co.) using the following solvent systems unless otherwise noted:
1) Solvent System 1
   chloroform
   methanol
   concentrated ammonium hydroxide
   2/2/1 v/v ratio
2) Solvent System 2
   chloroform
   methanol
   concentrate ammonium hydroxide
   12/4/1 v/v ratio $R_f$ values are reported using these solvent systems and commercially available Analtech silica plates (250 micron, Analtech Inc.).

All percentages are given in mole percents unless otherwise indicated.

Structural identification of compounds is indicated by reference to the compound numbers in the previous schemes.

Preparation of Starting Materials

EXAMPLE A

Synthesis of d,l-2-Bromo-4-(4-Nitrophenyl)-Butanoic Acid, t-Butyl Ester (Compound 1)

To a solution of 6 mL carbon tetrachloride and 15 mL thionyl chloride (0.2 mole) was added 12.5 g of 4-(4-nitrophenyl)butanoic acid (0.06 mole, FW=209.20) under a nitrogen atmosphere. The solution was brought to reflux for 1 hour with initial rapid liberation of hydrogen chloride and sulfur dioxide. N-bromosuccinimide (11.5 g, 0.062 mole) was then added as a slurry in 20 ml carbon tetrachloride and three drops of 48 percent aqueous hydrogen bromide catalyst were added to the warm solution whereupon bromine liberation was noted. The dark red solution was refluxed for an additional 35 minutes and at the end of this period, the red color discharged rapidly. A short path still head was attached to the pot and unreacted thionyl chloride and carbon tetrachloride were distilled off (a total of 30 mi). The solution in the pot was cooled and poured into dioxane (100 mi) with stirring. This dark solution was slowly added to 250 mL of a stirred solution of 8 percent aqueous dioxane. The dioxane was then removed on a rotary evaporator and 150 mL of methylene chloride was added to the dark oil followed by removal of this solvent on the rotary evaporator. Another 250 mL portion of methylene chloride was added, the solution was dried over magnesium sulfate and filtered. To this solution was added dicyclohexylcarbodiimide (14.4 g, 0.07 mole), 4-N,N-dimethylaminopyridine (0.7 g) and 10 mL t-butanol with stirring under a nitrogen atmosphere for 18 hours. TLC analysis (50:50 methylene chloride:carbon tetrachloride) revealed a new product ($R_f$=0.40 visual phosphomolybdic acid). The mixture was filtered to remove dicyclohexylurea and the resulting solution was extracted with 2×150 mL portions of water, 2×150 mL portions of 5 percent aqueous acetic acid, and 2×150 mL portions of water. The organic phase was dried over magnesium sulfate, filtered and the solvent was removed. The resulting oil was applied to a 1.5×14 inch column of flash silica gel which had been preeluted with a 50:50 mixture of methylene chloride:carbon tetrachloride to afford 1 (5.8 g, 0.169 mole) in 28 percent yield as a colorless oil the titled product d,1-2-bromo-4-(4-nitrophenyl)butanoic acid t-butyl ester. The product was characterized by:

$^1$H NMR (CDCl$_3$) δ 8.18 (d, 2H, J$_{ab}$=8.7 Hz), 7.38 (d, 2H, J$_{ab}$=8.7 Hz), 4.07 (dd, 1H, j$_1$=8.1 Hz, J$_2$=6.4 Hz methine H), 2.84 (m, 4H), 2.32 (m, 4H), 1.49 (s, 9H);

$^{13}$C NMR (CDCl$_3$) δ 168.9, 148.1, 146.9, 129.5, 124.0, 82.7, 46.3, 35.5, 33.0, 27.5;

IR (CDCl$_3$ film on NaCl plates) cm$^{-1}$ 2979, 2933, 1732 (ester), 1602, 1520, 1346, 1142.

EXAMPLE B

Synthesis of 1,4,7,10-Tetraaza-1-N-(1-Carbo-t-Butoxy-3-(4-Nitrophenyl)Propyl) CyclodoDecane, Monohydrobromide Salt (Compound 3)

To a stirred solution of 1.90 g cyclen free base (compound 2, 1,4,7,10-tetraazacyclododecane) (10.5 mmol, FW =172.28) in 25 mL of pentene stabilized chloroform was added 3.44 g of bromide 1 (9.50 mmol corrected to 95 percent purity 1), prepared by the procedure of Example A, over a 5 minute period under a nitrogen atmosphere with stirring. The reaction solution was stirred for 48 hours at room temperature (T=25° C.) TLC analysis (12:4:1 - solvent system 2) revealed conversion to the monoalkylation product 1,4,7,10-tetraaza-1-N-(1-carbo-t-butoxy-3-(4-nitrophenyl)propyl) cyclododecane (R$_f$=0.79 ninhydrin, iodine, and ultraviolet active versus a minor, high R$_f$=0.81). The yellow chloroform solution was applied to a 1.5×14 inch flash silica gel column which had been preeluted with 10 percent methanol in chloroform. The oil was then eluted with this solvent until passage of a light yellow band and then solvent system 1 was applied. An orange band immediately preceeded the major UV active fraction which proved to be 3. The combined fractions containing this material were collected to afford the monohydrobromide salt of 3 as a thick oil (3.7 g, 7.67 mmol) in 80 percent yield. The oil was dissolved in a minimum amount of chloroform and this solution was triturated with ether to provide a gum which upon standing in this solvent became a white powder (decomposed between 70° to 110° C. to a brown oil) which proved to be analytically pure 3 upon vacuum drying, characterized by:

$^1$H NMR (CDCl$_3$) δ 8.13 (d, 2H, J$_{ab}$=8.6 Hz), 7.48 (d, 2H, J$_{ab}$=8.8 Hz), 3.71 (s, 3H), 3.23 (dd, 1H, J$_1$=8.2 Hz, J$_2$=6.3 Hz), 2.5–3.0 (m, 20 H), 2.65 (m, 2H), 1.46 (s, 9H);

$^{13}$C NMR (CDCl$_3$) δ 171.9, 149.7, 146.4, 129.6, 123.7, 81.4, 64.8, 48.9, 48.1, 46.6, 45.3, 45.4, 32.5, 30.5, 27.9;

IR (CDCl$_3$ film on NaCl plates) cm$^{-1}$ 2979, 2936 2844, 1718 (ester), 1602, 1519, 1457, 1343;

EXAMPLE C

Synthesis of 1,4,7,10-Tetraaza-1-N-(1-Carbo-t-Butoxy-3-(4-Nitrophenyl)Propyl)-Bis-4,7,-N,N-(Carbo-t-Butoxymethyl)-Cyclododecane, Monohydrobromide Salt (Compound 4)

To 21 mL of chloroform containing 386 mg of 5-butyl-bromoacetate (2.00 mmol) and 400 mg diisopropylethyl amine (3-1 mmol) was added 516 mg (1.00 mmol) of the hydrobromide salt of 3, prepared by the procedure of Example B, with stirring for 48 hours. The solvent was removed and the crude product was applied to a 1×6 inch flash silica gel column which had been preeluted with 5 percent methanol in chloroform. Isolation of the first UV active fractions (R$_f$=0.81 in solvent systems, R$_f$=0.51 in 10 percent methanol in chloroform) upon elution with this solvent provided 4 (211 mg, 0.28 mmol) as its hydrobromide salt in analytical purity. The compound was further characterized by:

$^1$H NMR (CDCl$_3$) δ 10.1 (broad s, 1H), 8.17 (d, 2H, J$_{ab}$=8.6 Hz), 7.46 (d, 2H, J$_{ab}$=8.8 Hz), 3.2–3.4 (m, 5H), 2.6–3.2 (m, 18 H), 2.13 (m, 1H), 1.98 (m, 1H), 1.50 (s, 9H), 1.44 (s, 9H), 1.43 (s, 9H);

$^{13}$C NMR (CDCl$_3$) δ 171.3, 170,7, 169.6, 149.2, 146.6, 129.4, 123.8, 82.0, 81.8, 81.5 66.9, 58.7, 51.5, 50.9, 49.6, 48.4, 47.7 46.9, 32.5, 31.2, 28.0, 27.9, 27.8;

IR (CDCl$_3$ film on NaCl plates) cm$^{-1}$ 2985, 1724 (ester), 1602, 1520, 1456, 1370, 1347, 1151;

EXAMPLE D

Synthesis of 1,4,7,10-tetraaza-1-N-(1-Carbo-t-Butoxy-3-(4-Nitrophenyl)Propyl)-Bis-4,7,-N,N-(Carbo-t-Butoxymethyl)-10-N-(Carboxamidomethyl)Cyclododecane (Compound 5) and Reduction of the Nitro Group To 1 mL of chloroform was added 89 mg (0.119 mmol) hydrobromide 4 as prepared in Example C, 21.3 mg (0.159 mmol, 1.23 equivalents) bromoacetamide and 80 mg (0.62 mmol, 5.2 eq) diisopropylethyl amine, the solution was then placed in a 5 mm NMR (nuclear magnetic resonance) tube. The NMR tube was placed in the NMR spectrometer (probe T=50° C.) and the disappearance of the quaternary carbons of 4, (82.0, 81.8, 81.5 ppm) was monitored. The corresponding increase in three new carbon quaternary signals for 5 (81.1, 80.7 80.5) was complete within five hours and characterized by:

$^1$H NMR (CDCl$_3$) δ 8.15 (d, 2H, J=8.4 Hz), 7.38 (d, 2H, J=8.4 Hz), 3.2–3.4 (m, 6H), 2.6–3.2 (m, 18 H), 2.13 (m, 1H), 1.85 (m, 1H), 1.48 (s, 9H), 1.46 (s, 9H), 1.41 (s, 9H);

$^{13}$C NMR (CDCl$_3$) δ 174.3, 171.6, 170.3, 149.3, 146.2, 129.1, 123.4, 81.0, 80.7, 80.4, 62.6, 57.0, 56.4, 56.1, 55.5, 55.0, 53.1, 52.8, 52.0, 51.6, 48.4, 46.0, 32.6, 31.0, 28.1, 27.9, 27.7.

The chloroform was evaporated from the chloroform solution of 5 and the remaining light-yellow glassy solid was dissolved in 10 mL of 70 percent ethanol in water. Palladium on carbon catalyst (100 mg, 10 percent Pd on carbon from Lancaster Synthesis Ltd.) was added under a nitrogen atmosphere and hydrogen gas was sparged through the stirred solution for 18 hours. The solution was filtered through a short pad of celite and the solvent was evaporated to provide the corresponding amino compound 5b as a white, glassy solid (150 mg crude containing Hunig base) characterized by:

IR (CDCl$_3$ film on NaCl plates) cm$^{-1}$ 3317, 2982, 2936, 1724 (ester), 1688 (amide), 1602, 1456, 1392, 1368, 1157.

EXAMPLE E 1,4,7,10-Tetraaza-1-N-(1-Carbo-t-Butoxy-3-(4-Nitrophenyl)Propyl)-7-N-(Carbo-t-Butoxy-Methyl)Cyclododecane (Compound 7), Monohydrobromide Salt In 12 mL of chloroform were dissolved 516 mg (1.00 mmol.) of 3 hydrobromide salt, as prepared in Example B, and 198 mg (1.00 mmol) t-butylbromoacetate under a nitrogen atmosphere, and the solution refluxed over night. The concentrated solution was applied to a 1×6 inch flash silica gel column which was eluted with 10 percent methanol in chloroform. Elution with this solvent provided a light yellow, opaque band which was isolated giving hydrobromide salt of 7 (230 mg, 0.38 mmol) as an inseparable 75:25 isomer mixture of 1,7:1,4 diester positional isomers of analytical purity in 38 percent yield (R$_f$=0.14 in 10 percent methanol in chloroform) characterized by:

$^1$H NMR (CDCl$_3$) δ 8.17 (d, 2H, J$_{ab}$=8.5 Hz), 7.52 (75 percent) and 7.31 (25 percent)(two d, 2H total, J$_{ab}$=8.8 Hz), 3.23 (t, 1H, J=6.4 Hz), 2.5-3.1 (m, 18H), 1.8-2.2 (m, 2H), 1.50 and 1.44 (two singlets for minor (25 percent) 1,4-diester t-butyl group), 1.46 and 1.39 (two singlets for major (75 percent) 1,7-diester t-butyl group)-the total integration for these four resonances was 9H;

$^{13}$C NMR (CDCl$_3$) δ 171.9, 171.3, 170.7, 169.8, 149.8, 149.0, 146.5, 129.6, 129.4, 123.8, 123.7, 82.1, 81.8, 81.6, 81.3, 65.9, 65.6, 57.0, 51.4, 49.3, 49.1, 47.1, 47.0, 44.5, 43.6, 32.5, 31.0, 30.8, 27.9, 27.8, 27.8;

IR (CDCl3 film on NaCl plates) cm$^{-1}$ 2979, 2942, 2856, 1724, 1602, 1520, 1456, 1354, 1152;

EXAMPLE F 1,4,7,10-Tetraaza-1-N-(1-Carbo-t-Butoxy-3-(4-Aminophenyl)Propyl)-7-N-(1-Carbo-t-Butoxymethyl)-Bis-4,10-N,N-(Carboxyamido-Methyl)Cyclododecane (Compound 9)

In 7 mL of chloroform were dissolved 175 mg (0.289 mmol) diester 7 82 mg (0.594 mmol), bromoacetamide and 116 mg (0.90 mmol) diisopropylethyl amine with stirring at 25° C. The solution was allowed to stir under a nitrogen atmosphere for 48 hours. After 48 hours the chloroform was removed on a rotary evaporator and the obtained light-yellow glass was dissolved in 10 mL of 70 percent ethanol in water. Palladium on carbon catalyst (120 mg, 10 percent Pd on carbon from Lancaster Synthesis Ltd.) was added under a nitrogen atmosphere and hydrogen gas was sparged through the stirred solution for 18 hours. TLC analysis (solvent system 1) revealed a ninhydrin positive, ultraviolet (254 nm) active spot. The solution was filtered through Celite and the solvent evaporated to give 143 mg of 9 as a white glass.

$^1$H NMR analysis of this material revealed two broadened doublets at 6.98 and 6.66 ppm, an indication of nitro group reduction.

IR (CDCl$_3$film on NaCl plates) cm$^{-1}$ 3310, 2980, 934, 2836, 1721 (ester), 1672 (amide), 1623, 1517, 1368, 1152.

EXAMPLE 1

Synthesis of 1,4,7,10-Tetraaza-1-N-(1-Carboxy-3-(4-Nitrophenyl)-Propyl)-Bis-4,7-N,N-(Carboxymethyl)-10-N-Carboxamidomethyl)-Cyclododecane (PA-DOTAMA) (Compound 6)

The crude amino derivative 5b (130 mg), prepared as described in Example D, was dissolved in 10 mL of concentrated hydrochloric acid and the solvent removed (temperature did not exceed 40°C at 10 mm to 0.1 mm) to give 6 as a white solid. The white solid was applied to a column of acid washed, flash silica gel (1×12 cm with 10 g of gel, Alltech Inc.) which had been eluted with 3:3:1 chloroform:methanol:concentrated ammonium hydroxide.

The triacidmonoamide 6 (R$_f$0.19 in same solvent) was obtained as a non-hygroscopic white solid (52 mg, 0.100 mmol) in 83 percent overall yield from 4. The isomer ratio was determined by HPLC analysis (95:5 of 0.05 M sodium acetate (pH=6):acetonitrile to 50:50 in 10 min, 1 mL min$^{-1}$ at 254 nm using a 100 mm Econosphere C18 column with guard) and indicated the material to be greater than 97 percent area purity. The NMR spectra of this material under the following conditions were consistent with a pair of diastereomeric amides which arise from restricted rotation about the C-N1 bond.

$^1$H NMR (D$_2$O with dioxane internal standard, pH=4.5, 30° C.) δ 7.21 (m, 2H), 7.01 (m, 2H), 1.8-3.9 (m, 27H):

$^{13}$C NMR (D$_2$O with dioxane internal standard, pH=4.5, 30° C.) δ 180.5, 180.0, 177.5, 177.3, 175.3, 174.9, 173.0, 142.9, 141.5, 137.3, 136.4, 132.9, 122.0, 121.6, 69.0 (dioxane), 65.1, 65.0, 58.9, 58.6, 58.5, 58.2, 54.6, 53.8, 53.2, 52.1, 51.6, 51.3, 50.7, 50.4, 49.7, 49.0, 48.7, 54.0 ("doublet"), 29.6, 29.1;

MS (FAB in "magic bullet" matrix) m/e (1 percent) 523 (100 percent, (M+H)$^+$), 545 (38 percent, (M+Na)$^+$), 561 (M+Ca-H)$^+$).

This material was used directly in subsequent chelation studies.

EXAMPLE 2

1,4,7,10-Tetra-1-N-(1-Carboxy-3-(4-AminoPhenyl)-Propyl)-7-N-(1-Carboxymethyl)-Bis-4,10-N,N-(Carboxamidomethyl)Cyclododecane (PA-DODADA) (Compound 10a/b)

Compound 9 (143 mg) as isolated in Example F was dissolved in 6 N hydrochloric acid and the solvent removed in vacuo (40° C., 10$^{-1}$ mm) after ten minutes. The obtained white solid was applied to a column of acid washed, flash silica gel (1 cm with 15 g of gel, Alltech Inc.) which had been eluted with 2:2:1 chloroform:methanol:concentrated ammonium hydroxide. The symmetrical 1,7-diacid (R$_f$=0.32 in same solvent) could not be preparatively separated from 1,4-diacid (R$_f$=0.20) under these conditions, and fractions containing both compounds were pooled to provide an 80:20 isomer mixture of 10 (80 mg, 0.134 mmol) in 58 percent overall yield from 7. The isomer ratio was determined by HPLC analysis (95:5 0.05 M ammonium citrate at pH=6:acetonitrile to 30:70 in 30 min, 1 mL min$^{-1}$ at 254 nm using a 100 mm Econosphere C18 column with guard) and indicated the material to be greater than 96 percent area purity:

MS(FAB in "magic bullet" matrix) m/e (1 percent) 522 (100 percent, (M+H)+), 544 (28 percent, (M+Na)+).

This material was used directly in subsequent chelation studies.

EXAMPLE 3

Preparation of [Lu(PA-DOTAMA)].

I Excess lutetium (Lu$^{3+}$) ion (400 μL of 5 mM Lu-(OAc)$_3$.4 H$_2$O in pH=6.0, 0.50 M sodium acetate) was added to a solution of PA-H(NH$_4$)$_2$DOTAMA (100 μL of 5 mM PA-H(NH$_4$)$_2$DOTAMA in distilled water). A HPLC chromatogram of the product contained two peaks (due to the formation of two diastereomers) with retention times of 3.53 and 3.66 min. (100 mm Econosphere C18 3 μ column, 95:5 to 30:70 in 10 min., pH=6.0, 0.05 M ammonium acetate:acetonitrile, 1 mi/-min, 254 nm, Hewlett-Packard 1090 liquid chromatograph). The free ligand, PA-H(NH$_4$)$_2$DOTAMA, had a retention time of 1.85 min.

EXAMPLE 4

Preparation of SCN-PA-DOTAMA

The starting amide, PA-H(NH4)2DOTAMA (23 mg), was dissolved in 3 mL of distilled water and thiophosgene (15.8 μL) was added. The mixture was mixed vigorously in a Mixxor ™ for approximately 2 minutes. Excess thiophosgene was extracted with three 1 mL portions of chloroform. The aqueous layer was added to 20 mL of acetonitrile and the solvent was removed on a rotary evaporator at room temperature. The solid was dried for 2 hours on a vacuum line at room temperature.

Fast atom bombardment mass spectrum, m/e 565 and 587 (positive ion, [M+H+]+ and [M+Na+]+, respectively) and m/e 563 and 585 (negative ion, [M-H+]− and [M-2H++Na+]−, respectively).

The product was dissolved in approximately 4 mL of distilled water and stored at −70° C.

EXAMPLE 5

Preparation of [Lu(SCN-PADOTAMA)

Lutetium trichloride (LuCl$_3$.6H$_2$O, 5.0 mg) was added to 1 mL of a SCN-PA-DOTAMA solution (prepared as described in Example 4) and the resulting solution was titrated, using a pH meter, to about pH=6.4 by the addition of 0.10 M sodium hydroxide. The solution was reduced to dryness on a rotary evaporator at room temperature and dried on a vacuum line. The HPLC retention times of the recovered products were 6.25 and 6.28 minutes (two diastereomers, 100 mm Econosphere ™ C18 3 μ column, 95:5 to 30:70 in 10 min., pH=6.0 0.05 M ammonium acetate:acetonitrile, 1 mL/min$^{-1}$, 254 nm, Hewlett-Packard 1090 liquid chromatograph).

Fast atom bombardment mass spectrum, m/e 737 and 759 (positive ion, [M+H+]+ and [M+Na+]+ respectively) and m/e 735 (negative ion, [M-H+]−).

EXAMPLE 6

Preparation of [Lu(PA-DODADA)]Cl

The starting amide, PA-(NH4)2DODADA (20 mg) as a mixture of isomers, and 14 mg of LuCl$_3$.6H$_2$O were dissolved in 2 mL of distilled water, pH =6.0. The solution was heated in an oil bath at 90° C. for 30 minutes. The solvent was then removed on a rotary evaporator and the sample dried in a vacuum oven at 50° C. A HPLC chromatogram of the product contained two peaks (due to the formation of multiple isomers) with retention times of 4.58 and 4.66 minutes (HPLC preferred as in Example 5). The free ligand, PA-(NH$_4$)$_2$DODADA (two isomers), had retention times of 2.88 and 3.12 min. Fast atom bombardment mass spectrum, m/e 694 (positive ion, M+) and m/e 692 and 729 (negative ion, [M+−2H+]− and [M+−H++Cl−]−).

EXAMPLE 7

Preparation of SCN-PA-DOTAMA-$^{177}$Lu

To a mixture of 25 μl of $^{177}$Lu (0.7 mM) in 0.05 N hydrochloric acid and 25 μl of HEPES buffer (1.0 M, pH 7.0) was added 4 μl of a SCN-PA-DOTAMA solution (5 mM in H$_2$O). This was vortexed for about 5 seconds, and was allowed to stand at room temperature for 5 minutes before purification on a PRP-1 Mini-Clean ™ (Trademark of Alltech Associates, Inc., Deerfield, Ill.) cartridge (80 λl). The yield of the SCN-PA-DOTAMA-$^{177}$Lu complex was around 75 percent determined by HPLC analysis on a GF-250 column (dupont ™ Zorbax Bio series, 9.4 mm ID×25 cm), eluted with a citrate buffer (0.25 M, pH 7-0) containing 10 percent acetonitrile. The HPLC system was equipped with UV (280 nm) and radioactive dual detectors (Spectro 757 UV detector from the Applied Biosystems Inc. CA, and HPLC Radioactive Detector of Berthold Analytical Inst., Germany).

To purify the 177Lu complex, the chelation mixture was loaded onto a PRP-1 cartridge, pretreated with 800 μl of acetonitrile, 400 pl of water and 800 μl of a wash buffer (10 percent acetonitrile in 50 mM carbonate, PH 9.5) after being washed with 800 μl of the same wash buffer, the SCN-PA-DOTAMA-$^{177}$Lu complex was eluted off in an acetonitrile-carbonate buffer (2:1) mixture. The first 50 μl of the eluent was discarded. The bulk of the desired product came off in the next 50 μl. The SCN-PA-DOTAMA-$^{177}$Lu complex was identified by comparison of the retention time on HPLC with that of an authentic sample prepared per Example 5.

EXAMPLE 8

Preparation of PA-DOTAMA-$^{177}$Lu F(ab')$_2$ CC49 Conjugate

F(ab')$_2$ CC49 was prepared by enzymatic digestion of IgG CC49 according to the procedure described by Lamoyi and Nisonoff, *J. Immunol. Methods*, 56, 235–243 (1983), exchanged into a carbonate buffer (50mM, pH 9.5) and concentrated to approximately 16 mg/mi. To 170 μl of the antibody solution (25 nmoles) was added 30 μl of the SCN-PA-DOTAMA-$^{177}$Lu complex (8.7 nmoles; 3.8 mCi) prepared as described in Example 7. This solution was vortexed for about 5 seconds and was allowed to stand at room temperature (about 22° C.) for 2 hours. The progress of the conjugation was followed by HPLC on a GF-250 column. Fifty-three percent of the $^{177}$Lu had become antibody bound with an average number of BFC per antibody estimated to be around 0.2 after two hours. Upon termination, the $^{177}$Lu labeled F(ab')$_2$ was purified by centrifugal gel filtration with a Sephadex G-25 column (2.2 ml; QS-2B of Isolab Inc., Akron, Ohio), on a dupont Sorval centrifuge (model RT 6000B at 2900 rpm) at 4° C. for 2 minutes.

The integrity of the $^{177}$Lu labeled F(ab')$_2$ was verified by HPLC on GF-250 (method of Sivakoff, *Bio Chrom.*, 1(1), 42–48 (1986), gel electrophoresis coupled with autoradiography and immunoreactivity by immunoradio-metric assay (IRMA).

EXAMPLE 9

Preparation of SCN-PA-DODADA-$^{177}$Lu Complex

PA-(NH$_4$)$_2$DODADA (4 μl of a 5 mM solution in water) was mixed with 25 μl of $^{177}$Lu (0.7 mM in 0.05 N hydrochloric acid). To this was added 25 pl of a HEPES buffer (1.0 M, pH 7). It was vortexed and heated at 90° C. in a sand bath for 30 minutes. The yield of chelation was 86 percent based on the $^{177}$Lu activity. The identification was made by comparison with an authentic sample prepared as described in Example 6.

The $^{177}$Lu chelate was derivatized by the addition of 10 μl of a thiophosgene solution (1 percent in acetonitrile) at room temperature. After allowing the reaction to continue for 5 to 15 minutes, the $^{177}$Lu-SCN-PA-DOTADA complex was purified on a PRP-1 Mini-Clean ™ cartridge as described in the Example 7.

EXAMPLE 10

Preparation of PA-DODADA-$^{177}$Lu Labeled F(ab')$_2$ CC49.

The conjugation of PA-DODADA-$^{177}$Lu to F(ab')$_2$ CC49 was prepared as described in Example 8. The rate of coupling of SCN-PA-DODADA-$^{177}$Lu to antibody was considerably faster than that observed for DOTAMA and DOTA (see PCT Application No. WO 89/02788), i.e., greater than 50 percent reaction in 1 hour, compared to about 37 percent for SCN-PA-DOTAMA-177Lu, and less than 30 percent for SCN-PA-DOTA-177Lu in the carbonate buffer (pH 9.5), at room temperature (22° C.) and antibody concentration of about 1.25×10$^{-4}$ M.

The integrity of the Lu-177 labeled antibody was verified by standard biochemical techniques as those described in Example 8.

EXAMPLE 11

Preparation of PA-DOTA-$^{177}$Lu Labeled F(ab')$_2$ CC49 - for Biodistribution Comparison The titled compound was prepared according to the procedure described in Examples 8 and 10 except that SCN-PA-DOTA was the starting bifunctional chelant. PA-DOTA was prepared as described in PCT Application No. WO 89/02788.

EXAMPLE 12

PA-DOTA-$^{177}$Lu, PA-DOTAMA-$^{177}$Lu and PA-DODADA-$^{177}$Lu labeled IgG CC49.

The whole antibody conjugates were prepared in the similar fashion as described in Examples 8, 10 and 11, except that intact monoclonal antibody CC49 (whole IgG) was used. Again, rates of coupling of the SCN-BFC chelates to the antibody are in order of SCN-PA-DODADA >SCN-PA-DOTAMA>SCN PA-DOTA.

EXAMPLE 13

In Vitro stability of $^{177}$Lu PA-DOTAMA and $^{177}$Lu PA-DODADA antibody conjugates The experiment was designed to test the stability of the $^{177}$Lu BFC complexes at lysosomal pH 4 through 5, or in the presence of other chelators such as diethylenetriaminepentaacetic acid (DTPA). Thus, the antibody conjugates prepared per Examples 8, 10 and 11 were incubated in acetate buffers (0.2 M; at pH 4, and pH 6), or in a DTPA solution (0.25 M, pH 7.4 in PBS) at room temperature and with the antibody concentration at about 10 μM. The loss of Lu-177 label from the antibody was determined by HPLC on a GF-250 column. The results, summarized in Table I and expressed as percent Lu-177 remained bound to the antibody, demonstrates comparable stability for the three conjugates derived from different BFC's.

TABLE I

Stability of Various $^{177}$Lu BFC-Antibody Conjugates (% Lu-177 remained antibody bound)

| Time, hr. | 0 | 18 | 48 | 72 |
|---|---|---|---|---|
| PA-DOTAMA | | | | |
| in acetate, pH 6 | 99.4 | 99.2 | 99.1 | 99.1 |
| in acetate, pH 4 | 99.4 | 98.4 | 98.6 | 98.9 |
| in DTPA/PBS | 99.4 | 99.4 | 99.3 | 99.3 |
| PA-DODADA | | | | |
| in acetate, pH 6 | 99.4 | 99.3 | 99.1 | 99.1 |
| in acetate, pH 4 | 99.4 | 97.8 | 97.4 | 97.4 |
| in DTPA/PBS | 99.4 | 99.4 | 99.5 | 99.5 |
| PA-DOTA (Comparative) | | | | |
| in acetate, pH 6 | 99.2 | 99.3 | 98.7 | 99.5 |
| in acetate, pH 4 | 99.2 | 99.1 | 99.2 | 99.1 |
| in DTPA/PBS | 99.2 | 99.5 | 99.6 | 99.9 |

EXAMPLE 14

Animal Biodistribution Studies of $^{177}$Lu-PA-DOTAMA, PA-DOTADA, and PA-DOTA labeled F(ab')$_2$ and IgG CC49.

In vivo localization of the $^{177}$Lu-BFC labeled antibody was determined in Balb/c mice (purchased from Charles River Breeding Laboratories) of approximately 4 weeks of age. Female Balb/c mice were each injected via tail vein with about 10 μCi $^{177}$Lu of labeled antibody (7 to 10 ηg) in 50 μl of PBS. The mice were sacrificed at various time intervals. After exsanguination, the selected organs/tissues were excised, weighed, and radioactivity was measured in a gamma counter. The counts per minute (CPM) of $^{177}$Lu in each tissue was determined and expressed as CPM per gram of tissue per injected dose multiplied by 100 (percent injected dose/gram). Results for the chelates PA-DOTA, PA-DOTAMA and PA-DODADA conjugated to CC49 F(ab')$_2$ are given in Tables II A, B and C.

TABLE IIA (Comparative)
Biodistribution of $^{177}$Lu Injected as [$^{177}$Lu-PA-DOTA-F(ab')$_2$] CC49 Percent Injected Dose/Gram (n = 5)

| | 5 Hr. | | 24 Hr. | | 47 Hr. | | 120 Hr. | |
|---|---|---|---|---|---|---|---|---|
| Organ | Avg. | Std. | Avg. | Std. | Avg. | Std. | Avg. | Std. |
| Blood | 26.36 | 2.16 | 5.14 | 0.63 | 1.50 | 0.15 | 0.10 | 0.03 |
| Liver | 12.60 | 1.22 | 10.93 | 0.87 | 9.39 | 0.56 | 4.36 | 0.46 |
| Spleen | 9.72 | 1.02 | 8.77 | 0.92 | 9.28 | 0.95 | 4.74 | 0.48 |
| Kidney | 56.63 | 7.85 | 98.12 | 11.56 | 89.90 | 2.73 | 35.19 | 5.44 |
| Femur | 2.94 | 0.94 | 3.25 | 0.41 | 2.71 | 0.32 | 1.23 | 0.12 |

TABLE IIB

Biodistribution of $^{177}$Lu Injected as [$^{177}$Lu-PA-DOTAMA-F(ab')$_2$] CC49 Percent Injected Dose/Gram (n = 5)

| | 5 Hr. | | 24 Hr. | | 47 Hr. | | 120 Hr. | |
|---|---|---|---|---|---|---|---|---|
| Organ | Avg. | Std. | Avg. | Std. | Avg. | Std. | Avg. | Std. |
| Blood | 24.28 | 0.59 | 5.22 | 0.31 | 1.28 | 0.20 | 0.10 | 0.01 |
| Liver | 11.28 | 0.67 | 11.25 | 1.08 | 8.02 | 1.00 | 4.06 | 0.30 |

TABLE IIB-continued

Biodistribution of $^{177}$Lu Injected as
[$^{177}$Lu-PA-DOTAMA-F(ab')$_2$]
CC49 Percent Injected Dose/Gram (n = 5)

| Organ | 5 Hr. Avg. | Std. | 24 Hr. Avg. | Std. | 47 Hr. Avg. | Std. | 120 Hr. Avg. | Std. |
|---|---|---|---|---|---|---|---|---|
| Spleen | 9.27 | 0.65 | 9.03 | 1.02 | 8.22 | 0.76 | 4.43 | 0.43 n = 4, a |
| Kidney | 64.03 | 6.31 | 104.96 | 7.82 | 87.25 | 8.30 | 39.41 | 1.11 |
| Femur | 2.73 | 0.34 | 2.85 | 0.35 | 2.17 | 0.51 | 0.90 | 0.05 n = 4, a | a One tissue value rejected due to Outlier Statistic > p-05 value

TABLE IIC

Biodistribution of $^{177}$Lu Injected as [$^{177}$Lu-PA-DODADA-F(ab')$_2$] CC49
Percent Injected Dose/Gram (n = 5)

| Organ | 5 Hr. Avg. | Std. | 24 Hr. Avg. | Std. | 47 Hr. Avg. | Std. | 120 Hr. Avg. | Std. |
|---|---|---|---|---|---|---|---|---|
| Blood | 25.85 | 2.20 | 4.69 | 0.07 n = 4, a | 0.99 | 0.17 | 0.13 | 0.01 |
| Liver | 12.37 | 1.02 | 11.20 | 0.84 | 8.94 | 0.58 | 4.45 | 0.45 |
| Spleen | 10.02 | 0.65 | 9.86 | 0.77 | 9.31 | 1.03 | 7.14 | 0.12 n = 4, a |
| Kidney | 65.55 | 1.15 n = 4, a | 108.91 | 8.29 | 95.49 | 5.78 | 47.48 | 3.61 |
| Femur | 3.83 | 0.36 | 3.25 | 0.19 n = 4, a | 2.60 | 0.23 | 1.53 | 0.24 | a One tissue value rejected due to Outlier Statistic > p-05 value

The results show the similarity among the PA-DOTA, PA-DOTMA and PA-DODADA bifunctional chelators with respect to biodistribution when conjugated to F(ab')$_2$ fragments of CC49. The data also show the lower uptake of $^{177}$Lu by bone for PA-DOTAMA F(ab')$_2$ conjugates as compared to PA-DOTA F(ab')$_2$ conjugates, especially at longer time points (120 hours).

Results of biodistribution of chelates conjugated to CC49 IgG is given in Tables II D and E.

TABLE IID (Comparative)
Biodistribution of $^{177}$Lu Injected as
[$^{177}$Lu-PA-DOTA-IgG] CC49
Percent Injected Dose/Gram (n = 5)

| Organ | 24 Hr. Avg. | Std. | 1 Week Avg. | Std. | 2 Week Avg. | Std. | 3 Week Avg. | Std. |
|---|---|---|---|---|---|---|---|---|
| Blood | 25.95 | 2.53 | 15.64 | 0.76 | 11.34 | 0.37 n = 4, a | 7.45 | 0.49 |
| Liver | 9.01 | 0.70 | 6.60 | 0.31 N = 4, a | 6.39 | 0.82 | 4.54 | 0.42 |
| Spleen | 8.39 | 0.74 | 8.30 | 1.18 | 7.70 | 1.35 | 6.08 | 0.44 |
| Kidney | 13.52 | 0.93 | 6.97 | 0.56 | 4.41 | 0.94 | 2.36 | 0.11 |
| Femur | 3.17 | 0.41 | 2.61 | 0.25 | 2.20 | 0.24 n = 4, a | 1.52 | 0.26 | a One tissue value rejected due to Outlier Statistic > p-05 value

TABLE IIE

Biodistribution of $^{177}$Lu Injected as
[$^{177}$Lu-PA-DOTAMA-IgG] CC49
Percent Injected Dose/Gram (n = 5)

| Organ | 24 Hr. Avg. | Std. | 1 Week Avg. | Std. | 2 Week Avg. | Std. | 3 Week Avg. | Std. |
|---|---|---|---|---|---|---|---|---|
| Blood | 27.74 | 1.01 | 16.78 | 2.33 | 13.10 | 1.90 | 5.31 | 0.65 |
| Liver | 8.93 | 0.80 | 7.59 | 0.96 | 5.76 | 0.95 | 4.31 | 0.15 n = 4, a |
| Spleen | 7.39 | 3.61 | 9.16 | 1.11 | 8.55 | 1.16 | 4.57 | 0.23 |
| Kidney | 19.08 | 1.44 | 7.27 | 0.21 n = 4, a | 4.62 | 0.58 | 2.17 | 0.26 |

TABLE IIE-continued

Biodistribution of $^{177}$Lu Injected as
[$^{177}$Lu-PA-DOTAMA-IgG] CC49
Percent Injected Dose/Gram (n = 5)

| Organ | 24 Hr. Avg. | Std. | 1 Week Avg. | Std. | 2 Week Avg. | Std. | 3 Week Avg. | Std. |
|---|---|---|---|---|---|---|---|---|
| Femur | 3.80 | 0.34 | 2.92 | 0.38 | 2.23 | 0.89 | 0.83 | 0.28 | a One tissue value rejected due to Outlier Statistic > p-05 value

The data show the lower uptake of the $^{177}$Lu by the bone by conjugates of PA-DOTAMA as compared to conjugates of PA-DOTA at longer time points (3 weeks).

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for the treatment of a disease state in a mammal which comprises administering to said mammal in effective amount of a pharmaceutical formulation comprising a conjugate with a pharmaceutically acceptable carrier wherein the conjugate is a compound of the formula

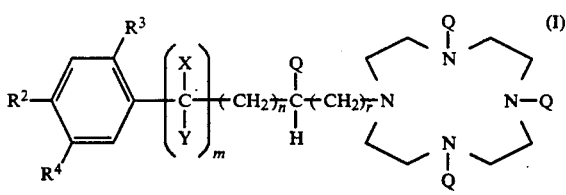

wherein:
each Q is independently hydrogen, $(CHR^5)_pCO_2R$; or $(CHR^5)_pC(O)N(R^6)_2$ with the proviso that at least one Q is $(CHR^5)_pC(O)N(R^6)_2$;
R at each occurrence is independently hydrogen, benzyl or $C_1$-$C_4$ alkyl;
each $R^5$ independently is hydrogen, $C_1$-$C_4$ alkyl or -($C_1$-$C_2$ alkyl)phenyl;
each $R^6$ independently is hydrogen, $C_1$-$C_9$ alkyl or -($C_1$-$C_2$ alkyl)phenyl;
X and Y are each independently hydrogen or may be taken with an adjacent X and Y to form an additional carbon-carbon bond to produce an alkene or alkyne;
n is 0 or 1;

m is an integer from 0 to 10 inclusive;

p=1 or 2;

r=0 or 1;

with the proviso that n is only 1 when X and/or Y form an additional carbon-carbon bond;

$R^2$ and $R^4$ are independently hydrogen, amino, isothiocyanato, semicarbazido, thiosemicarbazido, maleimido, bromoacetamido or carboxyl;

$R^3$ is $C_1$-$C_4$ alkoxy, —$OCH_2CO_2H$, hydroxy or hydrogen;

with the proviso that $R^2$ and $R^4$ cannot both be hydrogen but one of $R^2$ and $R^4$ must be hydrogen; or a pharmaceutically acceptable salt thereof;

complexed with an ion of a metal selected from $^{153}Sm$, $^{166}Ho$, $^{90}Y$, $^{149}Pm$, $^{159}Gd$, $^{140}La$, $^{177}Lu$, $^{175}Yb$, $^{47}Sc$ or $^{142}Pr$ and covalently attached to an antibody or antibody fragment.

2. A method for the treatment of a disease state in a mammal which comprises administering to said mammal an effective amount of the formulation of claim 1 wherein the antibody or antibody fragment is a monoclonal antibody or fragment thereof.

3. The method of claim 1 wherein the disease state is cancer.

4. A method for the diagnosis of a disease state in a mammal which comprises the steps of (a) administering to said mammal an effective amount of a pharmaceutical formulation comprising a conjugate with a pharmaceutically acceptable carrier wherein the conjugate is a compound of the formula

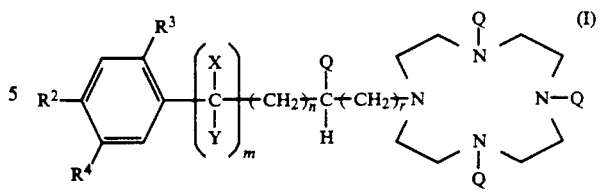

wherein:

each Q is independently hydrogen, $(CHR^5)_pCO_2R$; or $(CHR^5)_pC(O)N(R^6)_2$ with the proviso that at least one Q is $(CHR^5)_pC(O)N(R^6)_2$;

R at each occurrence is independently hydrogen, benzyl or $C_1$-$C_4$ alkyl;

each $R^5$ independently is hydrogen, $C_1$-$C_4$ alkyl or -($C_1$-$C_2$ alkyl)phenyl;

each $R^6$ independently is hydrogen, $C_1$-$C_9$ alkyl or -($C_1$-$C_2$ alkyl)phenyl;

X and Y are each independently hydrogen or may be taken with an adjacent X and Y to form an additional carbon-carbon bond to produce an alkene or alkyne;

n is 0 or 1;

m is an integer from 0 to 10 inclusive;

p=1 or 2;

r=0 to 1;

with the proviso that n is only 1 when X and/or Y form an additional carbon-carbon bond;

$R^2$ and $R^4$ are independently hydrogen, amino, isothiocyanato, semicarbazido, thiosemicarbazido, maleimido, bromoacetamido or carboxyl;

$R^3$ is $C_1$-$C_4$ alkoxy, —$OCH_2CO_2H$, hydroxy or hydrogen;

with proviso that $R^2$ and $R^4$ cannot both be hydrogen but one of $R^2$ and $R^4$ must be hydrogen; or a pharmaceutically acceptable salt thereof;

complexed with an ion of a radioisotope selected from $^{153}Sm$, $^{166}Ho$, $^{90}Y$, $^{149}Pm$, $^{159}Gd$, $^{140}La$, $^{177}Lu$, $^{175}Yb$, $^{47}Sc$ or 142Pr and covalently attached to an antibody or antibody fragment; and (b) utilizing a radiation detection means to detect and locate radiation from the conjugate.

5. The method of claim 4 wherein the antibody or antibody fragment is a monoclonal antibody or fragment thereof.

6. The method of claim 5 wherein the disease state is cancer.

* * * * *